US009449386B2

(12) United States Patent
Ma

(10) Patent No.: US 9,449,386 B2
(45) Date of Patent: Sep. 20, 2016

(54) METHOD AND APPARATUS FOR EXTENDED PHASE CORRECTION IN PHASE SENSITIVE MAGNETIC RESONANCE IMAGING

(71) Applicant: Board of Regents, The University of Texas System, Austin, TX (US)

(72) Inventor: Jingfei Ma, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 205 days.

(21) Appl. No.: 14/380,972

(22) PCT Filed: Feb. 27, 2013

(86) PCT No.: PCT/US2013/027994
§ 371 (c)(1),
(2) Date: Aug. 26, 2014

(87) PCT Pub. No.: WO2013/130587
PCT Pub. Date: Sep. 6, 2013

(65) Prior Publication Data
US 2015/0161784 A1    Jun. 11, 2015

Related U.S. Application Data

(60) Provisional application No. 61/604,413, filed on Feb. 28, 2012.

(51) Int. Cl.
*G06T 7/00* (2006.01)
*G01R 33/48* (2006.01)
(Continued)

(52) U.S. Cl.
CPC ......... *G06T 7/0012* (2013.01); *G01R 33/4828* (2013.01); *G01R 33/565* (2013.01);
(Continued)

(58) Field of Classification Search
None
See application file for complete search history.

(56) References Cited

U.S. PATENT DOCUMENTS 6,091,243 A    7/2000  Xiang et al.
6,192,263 B1   2/2001  Ma et al.
(Continued)

OTHER PUBLICATIONS

Ma, "Breath-hold water and fat imaging using a dual-echo two-point Dixon technique with an efficient and robust phase-correction algorithm," Magn Reson Med, 52(2):415-419, 2004.*

(Continued)

*Primary Examiner* — Bhavesh Mehta
*Assistant Examiner* — Menatoallah Youssef
(74) *Attorney, Agent, or Firm* — Parker Highlander PLLC

(57) ABSTRACT

Methods, apparatuses, systems, and software for extended phase correction in phase sensitive Magnetic Resonance Imaging. A magnetic resonance image or images may be loaded into a memory. Two vector images A and B associated with the loaded image or images may be calculated either explicitly or implicitly so that a vector orientation by one of the two vector images at a pixel is substantially determined by a background or error phase at the pixel, and the vector orientation at the pixel by the other vector image is substantially different from that determined by the background or error phase at the pixel. A sequenced region growing phase correction algorithm may be applied to the vector images A and B to construct a new vector image V so that a vector orientation of V at each pixel is substantially determined by the background or error phase at the pixel. A phase corrected magnetic resonance image or images may be generated using the vector image V, and the phase corrected magnetic resonance image or images may be displayed or archived.

20 Claims, 8 Drawing Sheets

(51) Int. Cl.
*G01R 33/565* (2006.01)
*G06K 9/46* (2006.01)
*G06T 5/00* (2006.01)
*A61B 5/055* (2006.01)
*G01R 33/56* (2006.01)

(52) U.S. Cl.
CPC ............... *G06K 9/46* (2013.01); *G06T 5/00* (2013.01); *A61B 5/055* (2013.01); *G01R 33/5602* (2013.01); *G01R 33/5607* (2013.01)

(56) References Cited

U.S. PATENT DOCUMENTS

| | | | |
|---|---|---|---|
| 7,227,359 | B2 | 6/2007 | Ma |
| 7,888,936 | B2 | 2/2011 | Jellus |
| 2005/0165296 | A1 | 7/2005 | Ma et al. |
| 2009/0112081 | A1 | 4/2009 | Yu et al. |
| 2010/0195885 | A1 | 8/2010 | Ma et al. |

OTHER PUBLICATIONS

Ma, "Two-point Dixon imaging with flexible echo times and a region growing-based postprocessing algorithm," Proc. Intl. Soc. Mag. Reson. Med., 19:2707, 2011.*

Berglund et al., "Two-point Dixon method with flexible echo times," *Magnetic Resonance in Medicine*, 65(4):994-1004, 2011.

Eggers et al., "Dual-echo Dixon imaging with flexible choice of echo times," *Magnetic Resonance in Medicine*, 65(1):96-107, 2011.

Eggers et al., "Dual-echo Dixon imaging with unrestricted choice of echo times," *Proc. Intl. Soc. Mag. Reson. Med.*, 18:770, 2010.

Eggers, "Influence and compensation of fat signal dephasing and decay in two-point Dixon imaging," *Proc. Intl. Soc. Mag. Reson. Med.*, 18:2924, 2010.

Ma et al., "Fat-suppressed three-dimensional dual echo Dixon technique for contrast agent enhanced MRI," *J Magn Reson Imaging*, 23(1):36-41, 2006.

Ma, "Two-point Dixon imaging with flexible echo times and a region growing-based postprocessing algorithm," *Proc. Intl. Soc. Mag. Reson. Med.*, 19:2707, 2011.

PCT International Preliminary Report on Patentability issued in International Application No. PCT/US2013/027994, mailed Sep. 12, 2014.

PCT International Search Report and Written Opinion issued in International Application No. PCT/US2013/027994, mailed Jun. 25, 2013.

Xiang, "Two-point water-fat imaging with partially-opposed-phase (POP) acquisition: an asymmetric Dixon method," *Magn Reson Med.*, 56(3):572-584, 2006.

* cited by examiner

METHOD AND APPARATUS FOR EXTENDED PHASE CORRECTION IN PHASE SENSITIVE MAGNETIC RESONANCE IMAGING

CROSS REFERENCE TO RELATED APPLICATIONS

This application is a national phase application under 35 U.S.C. §371 of International Application No. PCT/US2013/027994, filed Feb. 27, 2013, which claims priority to U.S. Provisional Patent Application Ser. No. 61/604,413, filed Feb. 28, 2012, the entire disclosure of each of which is incorporated herein by reference.

BACKGROUND

1. Field of the Invention

The present invention relates generally to the field of medical imaging. More particularly, embodiments of the invention relate to phase sensitive magnetic resonance imaging (MRI) using an extended phase correction algorithm, which among other things can process images with more flexible phases for successful water and fat imaging.

2. Description of Related Art

MRI has proven useful in the diagnosis of many diseases such as hepatic steatosis, cancer, multiple sclerosis, sports related injury, and bone marrow disorders. MRI provides unique imaging capabilities that are not attainable in any other imaging method. For example, MRI can provide detailed images of soft tissues, abnormal tissues such as tumors, and other structures that cannot be readily imaged using techniques like X-rays. Further, MRI operates without exposing patients to ionizing radiation experienced in X-rays. For these and other reasons, MRI is commonly utilized in medical and other fields.

In comparison to other imaging modalities, MRI is unique in that an MRI signal is represented by a complex number, rather than simply a scalar (such as X-ray attenuation in Computed Tomography). The image value for each image pixel, therefore, usually includes a magnitude and a phase. Although the phase of an image pixel may carry important information and may be used in many applications such as chemical shift imaging, thermal imaging, and blood flow quantification, it is usually discarded in a standard image reconstruction process. An underlying reason is that some unwanted background or error phase almost always accompanies the desired phase.

One application for phase correction of MR images includes inversion recovery imaging. Inversion recovery (IR) is generally used as a magnetization preparation technique in MRI. In IR imaging, a longitudinal magnetization along a main magnetic field is first rotated to the opposite direction using a 180 degree radiofrequency (RF) pulse. The inverted magnetization can be recovered by T1 relaxation during an inversion time (TI) between the inversion and the excitation RF pulse. One example application of IR imaging is for suppression of a given type of tissue with a characteristic T1, such as short-tau inversion recovery (STIR) for fat suppression or fluid-attenuated inversion recovery (FLAIR) for cerebral spinal fluid attenuation. Another example application of IR imaging is for increased tissue contrast from the doubling of the dynamic range of the longitudinal magnetization. The latter application could be useful for imaging of neonate brains, myocardium at delayed enhancement, or for evaluating pulmonary blood flow.

The potential for increased tissue contrast by IR imaging, however, is not always realized because conventional MR image reconstruction preserves only the magnitude of the MR signals and may actually lead to reduced or even reversed contrast in an IR image.

Phase-sensitive IR (PSIR) image reconstruction, in which unwanted background or error phase in an IR image is removed, is a technique that can restore the contrast loss or reversal resulting from conventional magnitude image reconstruction. One challenge in PSIR image reconstruction is a phase-correction process to separate the intrinsic signal phase in the complex image from the background or error phase, which is almost unavoidable in an MR image. Several approaches have been proposed for PSIR image reconstruction including calibration of the phase errors through acquisition of another image without IR or with IR at different TIs. However, these approaches reduce data acquisition efficiency. Further, spatial misregistration between the actual and calibration scans due to patient motion can also be problematic.

An alternative approach for PSIR image reconstruction is to determine the background or error phase from the IR image itself using various phase correction algorithms. In general, only the signal phase of a neighbor pixel for overall phase correction is used in many of these phase correction algorithms. As such, pixels with large phase variation, such as in regions of low signal-to-noise ratio (SNR) or along tissue boundaries may corrupt the phase correction process. In order to minimize the effect, an empirical threshold is usually selected to exclude regions of large phase uncertainty. The actual threshold value, however, can be critical. If the value selected is too small, phase correction cannot reach beyond the regions defined by the threshold value and may thus be terminated prematurely. Alternatively, if the value selected is too large, errors in phase correction may propagate and even corrupt the rest of the process. In a region growing-based approach, for example, the selection of the threshold value together with that of the initial seed and the path of the region growing, determines the quality and the scope of the phase correction. To allow phase correction to proceed beyond local phase fluctuations and to avoid potential corruption due to phase correction errors, an additional ad hoc treatment, such as a "bridge filter" is required. Another limitation of the phase correction algorithms is the global polarity of a PSIR image, which cannot be unambiguously determined from the phase correction process itself. Consequently, images from different component channels of a phased array coil cannot be readily combined and inconsistency in display may arise for different images of a multi-slice acquisition.

Another application where correction of phase errors may be important is the Dixon chemical shift imaging technique. In MRI, the signal-emitting protons may resonate at different Larmor frequencies because they have different local molecular environments or chemical shift. The two most distinct species found in the human body are water and fat, whose Larmor frequencies are separated by about 3.5 ppm (parts per million). In many clinical MRI applications, it is desirable to suppress signals from fat because they are usually very bright and obscure lesions. Presently, a commonly used method for fat suppression is chemical shift selective saturation (CHESS), which, despite its many advantages, is known to be intrinsically susceptible to both radiofrequency (RF) and magnetic field inhomogeneity. Another technique that is sometimes used for fat suppression is the short tau inversion recovery (STIR), which is based on the characteristically short T1 relaxation constant for fat, rather than on its Larmor frequency. The drawbacks of STIR include reduction in scan efficiency and signal-to-noise ratio as well as potential alteration to the image contrast.

In U.S. Pat. No. 7,227,359, which is incorporated herein by reference, the present inventor described, among other things, region growing based phase correction methods for phase sensitive MRI. Potential applications for such methods include a two-point Dixon method for water and fat imaging. In a typical two-point Dixon method, two acquired input images have water and fat relative phase angles of approximately 0° (in phase) and approximately 180° (opposed phase), respectively. This restriction of relative phase angles, in turn, imposes certain restrictions on corresponding echo times that are used for acquiring input images.

In the article Xiang, Magnetic Resonance in Medicine 56:572-584, 2006, which is incorporated herein by reference, Xiang proposed that it is possible to do water and fat imaging using two input images acquired at more flexible echo times (e.g., phases that are not substantially equal to 0° and 180°). In that article, Xiang discussed an iterative phase correction method and demonstrated water and fat imaging using an input image that is in phase and another input image that has a more flexible phase. Xiang called the iterative phase correction method RIPE, which stands for Regional Iterative Phasor Extraction. RIPE fundamentally relies on a global convergence of local statistical iterations of different phasor candidates in different regions of an image. Potential limitations of the approach include a requirement for prior image thresholding to successfully exclude low signal-to-noise regions. The RIPE approach may also run into difficulties when two input images are substantially in-phase and substantially 180° out-of-phase, or when regions of large artifacts (e.g., near metallic implants) are present to create an incorrect initial bias for the phasor iterations. Further, the fat signal is modeled as a single spectral resonance with no attenuation as a function of the echo time in Xiang's 2006 Magnetic Resonance in Medicine 56:572-584 implementation of the RIPE approach for two-point Dixon imaging.

More recently in Eggers et al, abstract, 2010 Annual Scientific Meeting of the International Society of Magnetic Resonance in Medicine, and Magnetic Resonance in Medicine 65(1):96-107, 2011, which are incorporated herein by reference, Eggers et al. reported that by using the RIPE method, two input images can both be relaxed to have flexible phases that are substantially different from in-phase and substantially different from 180° out-of-phase. Further, the fat signal model is extended to include up to 7 separate spectral resonance peaks, which are determined from measurements using magnetic resonance spectroscopy.

The increased flexibility associated with the use of images having echo times that are more flexible than being substantially in-phase and substantially 180° out-of-phase can reduce some restrictions of scan parameters and further improve the scan efficiency for techniques such as dual-echo acquisition. This flexibility, however, also adds additional variables and complexity to phase error calculations that were not considered in previous algorithms. For example, in the above-referenced publications both by Xiang and by Eggers et al, the important step of phase correction in postprocessing images with flexible echo times has—prior to embodiments of the present disclosure—been based on a statistical iterative process that is named RIPE by Xiang. This process involves empirical image thresholding to exclude low signal-to-noise regions. The process may also run into difficulties when two input images are substantially in-phase and substantially 180° out-of-phase, or when regions of large artifacts (e.g., near metallic implants) are present to create an incorrect initial bias for the phasor iterations. Furthermore, modeling of the fat signal by Eggers et al. is based on measurement using magnetic resonance spectroscopy that can only account for limited number of spectral peaks and cannot account for other confounding factors such as magnetic field strength, pulse sequence and scan parameters used, and potentially different relaxation times for the different spectral peaks. Embodiments of the present disclosure relate generally to alternative post-processing strategies for phase sensitive magnetic resonance imaging. When applied to two point Dixon imaging, certain embodiments of the present disclosure use a generalized signal model for fat and feature a particular type of sequenced region-growing scheme that accounts for additional complexities, without a need for image thresholding or a statistical iterative processing. Further, the disclosed sequenced region growing scheme may naturally encompass input images that are acquired substantially in-phase and substantially 180° out-of-phase, and is not affected by the presence of regions with large image artifacts. Using this post-processing strategy, successful water and fat separation can be accomplished with, for example, phantom and in vivo images by a 3D dual-echo acquisition with flexible echo times. Post-processing strategies of the present disclosure can also be directly applied to other useful applications such as, but not limited to, phase sensitive inversion recovery image, single point Dixon imaging, and single point silicone-specific imaging. In general, embodiments of this disclosure provide, in part, a new sequenced region growing algorithm that is able to correct background or error phase in acquired magnetic resonance image or images.

Referenced shortcomings of some existing or traditional approaches to phase sensitive MRI are not intended to be exhaustive, but rather are among many that tend to impair the effectiveness of previously known techniques concerning image reconstruction; however, those mentioned here are sufficient to demonstrate that the methodologies appearing in the art have not been satisfactory and that a need exists for techniques described and claimed in this disclosure.

SUMMARY OF THE INVENTION

Certain shortcomings of the prior art may be reduced or eliminated by some or all of the techniques disclosed here. These techniques are applicable to a vast number of MRI applications, including but not limited to any such application involving two-point Dixon imaging techniques with flexible echo times.

Embodiments of the disclosure may present an alternative postprocessing strategy that uses a generalized signal model and features a particular type of sequenced region growing scheme (which can be fully automated) without a need for image thresholding. As demonstrated below, using such embodiments, one can realize more successful water and fat separation. For example, water and fat separation has been achieved with phantom and in vivo images by a 3D dual-echo acquisition with flexible echo times. The sequenced region growing scheme of the present disclosure, which can handle input images with more flexible phases, can lead to a wide range of applications in phase-sensitive MRI, as will be recognized by those having ordinary skill in the art. As but one example: because of the increase in flexibility associated with input images having flexible echo time, a less efficient dual echo image acquisition with unipolar flyback readout gradients may be used as a practical alternative to a more efficient bipolar acquisition given its advantage of having no off-resonance related spatial misregistration between the two input images along a frequency-encode direction. As an another example, a triple-echo readout that maximizes the data acquisition efficiency in a fast spin echo pulse sequence, or in a spin echo pulse sequence, or in a balanced steady state free precession sequence, may be used to acquire three images in a single acquisition. In this case, the two images from the $1^{st}$ echo and the $2^{nd}$ echo may be processed to generate one set of water-only and fat-only images, and the two images from the $2^{nd}$ echo and the $3^{rd}$ echo may be processed to generate a second set of water-only and fat-only images. The two sets of water-only and fat-only images may be combined to yield a final set of water-only and fat-only images with improved signal-to-noise ratio.

In one respect, embodiments of the present disclosure involve methods for phase-sensitive MRI to separate an intrinsic signal phase from a coexistent background or error phase, which could be due to field inhomogeneity or other system imperfections. For many applications, such as Dixon chemical shift imaging and phase sensitive inversion recovery imaging, the background or error phase usually varies slowly in space from pixel to pixel. The intrinsic phase, on other hand, may be determined by tissue distribution and can have sudden spatial changes. The sequenced region growing methods disclosed here are able to handle background or error phase correction in the presence of regions of low signal-to-noise ratio and/or of large image artifacts, and is in general applicable to applications such as Dixon water and fat imaging with flexible echo times or single-point Dixon silicone specific imaging.

In another respect, methods are provided that include steps for acquiring a plurality of MRI data signals and forming complex images from the data signals. In some embodiments, the data may be acquired from multiple slices, multiple receiver coils, or even at different time points as dynamic series. Further, a pulse sequence and a partially parallel imaging technique, such as a sensitivity encoding (SENSE) technique, may be performed to acquire the data. The data may be an opposed-phase echo and an in-phase echo of a first and second signal data, or it may have flexible phases that do not have in- and opposed-phases. In some embodiments, the echo may be acquired by performing a gradient-echo dual-echo sequence (e.g., a two-dimensional gradient-echo dual-echo sequence or a three-dimensional gradient-echo dual-echo sequence). In other embodiments, the echo may be acquired by performing a two-dimensional spin echo pulse sequence. Alternatively, the echo may be acquired by performing a fast spin echo sequence (e.g., a two-dimensional sequence or three-dimensional fast spin echo sequence), a spin echo sequence, or a balanced steady state free precession sequence (e.g., a two-dimensional or a three-dimensional sequence). In the fast spin echo, spin echo, or balanced steady state free precession sequences, it may be preferable to use a triple echo readout for maximal data acquisition efficiency. In some respects, data may be acquired from an inversion recovery pulse sequence. The data may be acquired from an inversion recovery fast spin echo sequence (e.g., two-dimensional sequence or three-dimensional fast spin echo sequence). Alternatively, the data may be acquired from an inversion recovery two-dimensional or three-dimensional gradient echo sequence.

In other respects, data may be acquired from a one-point Dixon echo, which includes water and fat signals or further includes silicone signals. In one embodiment, the one-point Dixon data may be acquired from a gradient-echo sequence with a flexible echo time (e.g., two-dimensional or three-dimensional gradient-echo sequence). In other embodiments, one-point Dixon data may be acquired by time-shifting conventional spin echo, such as in a two-dimensional spin echo sequence. Alternatively, the one point Dixon data may be acquired from a two-dimensional or three-dimensional fast spin echo sequence. Further, the one point Dixon data may be acquired with an echo shift in any of the pulse sequences so that water and fat signals are substantially in-phase and the silicone signal is substantially out-of-phase with the water and fat signals. Subsequent processing using the disclosed methods allow for the generation of silicone-only images and silicone-suppressed images.

Certain embodiments of the present disclosure involve a particular type of sequenced region growing process that may be followed with algebraic calculations, which can yield a fat-only image and a water-only image in the case of Dixon chemical shift imaging. Alternatively, phase sensitive inversion recovery image can be taken as the real part of a phase corrected inversion recovery image. These images may then be displayed or archived using output and storage devices. Other uses for flexible phase processing include imaging of silicone, such as in breast imaging of silicone breast implants.

In other respects, systems or apparatuses are disclosed. Embodiments of a system may include a magnetic resonance imaging (MRI) scanner capable of running a pulse sequence such as a fast gradient-echo dual-echo sequence, a controller, and an output device. The MRI scanner may be adapted to provide a plurality of data signals following a scan. Using a pulse sequence such as the fast gradient-echo dual-echo pulse sequence, a plurality of data signals may be produced, collected, and sent to the controller for processing. The controller may receive the data signals and implement image reconstruction and a phase correction algorithm to produce an image or images (e.g., a water-only image, a fat-only image, etc). The system may additionally include a processor and a memory comprising machine executable code configured to perform image processing steps.

In one respect, embodiments of this disclosure may involve a computerized method for generating a phase corrected magnetic resonance image or images. A magnetic resonance image or images containing background or error phase information is acquired. Two vector images A and B are calculated either explicitly or implicitly using the acquired image or images so that a vector orientation by one of the two vector images at a pixel is substantially determined by the background or error phase at the pixel, and the vector orientation at the pixel by the other vector image is substantially different from that determined by the background or error phase at the pixel. A sequenced region growing phase correction algorithm is applied to the vector images A and B to construct a new vector image V, wherein the algorithm includes:

(i) selecting an initial seed pixel or pixels and assigning either A or B of the initial seed pixel or pixels as a value of V for the initial seed pixel or pixels;

(ii) selecting a secondary seed pixel and selecting either A or B of the secondary seed pixel as a value of V for the secondary seed pixel based on whether A or B of the secondary seed pixel has a smaller angular difference with an estimated V for the secondary seed pixel;

(iii) determining for the secondary seed pixel a local quality metric for each of the nearest neighbor pixels of the secondary seed pixel for which V has not been determined and assigning a priority to each of the nearest neighbor pixels using the local quality metric in order to determine the sequence by which each of the nearest neighbor pixels is to be selected as a further seed pixel; and (iv) repeating the steps of (ii) and (iii) to complete the sequenced region growing with respect to further seed pixels and to construct the vector image V so that a vector orientation of V at each pixel is substantially determined by the background or error phase at the pixel.

The phase corrected magnetic resonance image or images may be generated from the acquired magnetic resonance image or images using the vector image V, and the phase corrected magnetic resonance image or images may be displayed or archived.

In other respects, embodiments may involve correcting vector images A and B with a global linear error phase correction along one or more dimensions prior to performing the sequenced region growing. A low-pass filter may be applied to vector image V before generating the phase corrected magnetic resonance image or images. Amplitudes of the vector images A and B at a pixel may be weighted by a signal amplitude at the pixel. An initial seed pixel or pixels may be selected from a high-quality region, where high-quality includes a predetermined signal-to-noise ratio or a predetermined local orientational coherence for the vector images A or B. An initial seed pixel or pixels and the value of V at the initial seed pixel or pixels may be selected based on an orientational coherence of either A or B at the initial seed pixel or pixels with V at a spatially or temporally neighboring pixel or pixels of a spatially or temporally neighboring image for which V is already known or has been determined. An initial seed pixel or pixels may be placed onto a high priority pixel stack or stacks among a series of pixel stacks that are initially empty and which facilitate a sequencing of the sequenced region growing. A pixel may be selected as a secondary seed pixel if it has not been processed previously as a seed pixel and it is on a pixel stack that has a highest priority among pixel stacks that contain at least one pixel that has not been processed as a seed pixel.

In other respects, embodiments may involve a local quality metric of a pixel being calculated as the smaller of two orientational differences between A and B of the pixel with an estimated V for the pixel. The estimated V for the pixel may be a zeroth order estimation calculated as an average of V for pixels located within a neighboring region of the pixel and for which V has been previously determined. The estimated V for the pixel may be a first order estimation that includes an average and a linear expansion of V for pixels that are located within a neighboring region of the pixel and for which V has been previously determined A size of the neighboring region may be either fixed or adaptively adjusted based on a local quality metric for the pixel. The maximum possible range of $0$-$\pi$ for the angular difference between any two vectors may be used to gauge and bin the local quality metric and to place a pixel onto a pixel stack. The pixel stack covering a subrange of $0$-$\pi$ for the quality metric may be assigned a priority, where a pixel stack of a higher priority is for receiving pixels with a smaller quality metric, and a pixel stack of a lower priority is for receiving pixels with a larger quality metric. The priority of a pixel stack from which a pixel is selected as a secondary seed pixel may be recorded for the sequenced region growing as a quality metric index to reflect an integrity of the sequenced region growing. The quality metric index may be used to automatically segment an image into different segments of possible inconsistent region growing and then to combine the different segments into an overall consistent region growing to form a final vector image V.

In other respects, embodiments may involve a value of the vector A for an initial seed pixel being assigned as $V_A$, and a sequenced region growing being performed to construct a vector image $V_A$, where a value of the vector B for the same initial seed pixel is assigned as $V_B$, and another sequenced region growing is performed to construct a vector image $V_B$. Either vector image $V_A$ or vector image $V_B$ may be set to a final vector image V, depending on whether vector image $V_A$ or vector image $V_B$ has a greater overall orientational smoothness.

In other respects, embodiments may involve the sequenced region growing being performed in two spatial dimensions. The sequenced region growing may be performed in three spatial dimensions. The sequenced region growing may be performed by including the temporal dimension for a series of dynamically acquired images.

In other respects, embodiments may involve acquiring two-point Dixon water and fat images, wherein a first image S1 is acquired at a first echo time TE1 and a second image S2 is acquired at a second echo time TE2. Acquiring two-point Dixon water and fat images may involve using dual-echo bipolar readout gradients. Acquiring two-point Dixon water and fat images may involve using dual-echo unipolar readout gradients. Acquiring two-point Dixon water and fat images may involve using triple-echo readout gradients. Acquiring two-point Dixon water and fat images may involve using interleaved single echo readout gradients.

In other respects, embodiments may involve selection of TE1 and TE2 being flexible except to avoid a small orientational difference between vector image A and vector image B. The images $S_1$ and $S_2$ may be expressed according to the following equations:

$$S_1 = (W + \delta_1 F e^{i\theta_1}) P_1$$

$$S_2 = (W + \delta_2 F e^{i\theta_2}) P_1 P$$

where W and F are amplitudes for water and fat respectively, $P_1$ is a phase factor of image $S_1$, P is an additional phase factor of image $S_2$ relative to image $S_1$ and is determined by a background or error phase, and one may determine by an image based pre-calibration an amplitude attenuation factor ($\delta_1$, $\delta_2$) and phase ($\theta_1$, $\theta_2$) as a function of two echo times (TE1, TE2) for the fat signal. Pre-calibration of ($\delta_1$, $\delta_2$) may be performed in part by determining an echo time dependence of a signal amplitude of a known fat-only image region, and pre-calibration of ($\theta_1$, $\theta_2$) may be performed in part by determining an echo time dependence of a phase discontinuity between a known fat-only image region and a neighboring known water-only region. The pre-calibration may be performed for a given pulse sequence, a scan protocol, or a magnetic field strength.

In other respects, embodiments may involve the images $S_1$ and $S_2$ being used to generate two vector images A and B as expressed according to the following equations:

$$A = S_1 * S_2 [Q_A + \delta_1(1-Q_A)e^{i\theta_1}]/[Q_A + \delta_2(1-Q_A)e^{-i\theta_2}]$$

$$B = S_1 * S_2 [Q_B + \delta_1(1-Q_B)e^{i\theta_1}]/[Q_B + \delta_2(1-Q_B)e^{-i\theta_2}]$$

where $Q_A$ and $Q_B$ are the two mathematically possible solutions of the following quadratic equation of Q, which is defined as $$Q = \frac{W}{W + F}$$

(i.e., the water fraction for a given pixel):

$$[(1+\delta_2^2-2\delta_2 \cos \theta_2)M_1-(1+\delta_1^2-2\delta_1 \cos \theta_1)M_2]Q^2-2[(\delta_2^2-\delta_2 \cos \theta_2)M_1-(\delta_1^2-\delta_1 \cos \theta_1)M_2]Q+[(M_1\delta_2^2-M_2\delta_1^2)]=0$$

where $M_1$ and $M_2$ are the square of the amplitudes of the images $S_1$ and $S_2$, respectively (i.e., $M_1=|S_1|^2$ and $M_2=|S_2|^2$). The vector images may be further normalized and weighted by a signal amplitude, such as:

$$A' = \frac{A}{|A|}\sqrt{M_1+M_2}$$

$$B' = \frac{B}{|B|}\sqrt{M_1+M_2}$$

where again, $M_1=|S_1|^2$ and $M_2=|S_2|^2$. Sequenced region growing may be used to construct a vector image V from the two vector images A and B. The vector image V may be used to phase correct and remove the phase factor P from the image $S_2$, the phase corrected $S_2$ may be combined with $S_1$ to solve for $WP_1$ and $FP_1$, and then to generate a water-only image and a fat-only image according to the following equations:

$$W=\text{Real}\{(WP_1)\overline{WP_1}^*/|\overline{WP_1}|\}$$

$$F=\text{Real}\{(FP_1)\overline{FP_1}^*/|\overline{FP_1}|\}$$

where Real{ ... } is to take the real component of its complex argument, * is to take the complex conjugate of its argument, and $\overline{WP_1}$ and $\overline{FP_1}$ represent low-pass filtering of $WP_1$ and $FP_1$, respectively.

In other respects, embodiments may involve acquiring a single-point Dixon water and fat image wherein a flexible echo time TE is used and the acquired magnetic resonance image is expressed as: $S=(W+Fe^{i\theta})P$, where $\theta$ is dependent on TE and the dependence is determined with an image-based pre-calibration, and P ($\equiv e^{i\phi}$) is a phase factor for the image S. The vector image A may be set to S and the vector image B may be set to $Se^{-i\theta}$. A sequenced region growing may be used to construct a vector image V from the two vector images A and B, the vector image V may be used to phase correct or remove P from S to form S', and a water-only image and a fat-only image may be generated according to:

$$F=\text{Imag}\{S'\}/\sin \theta$$

$$W=\text{Real}\{S'-F \cos \theta\}$$

where Real{ ... } and Imag{ ... } are to take the real and imaginary components of their component, respectively.

In other respects, embodiments may involve acquiring a single-point silicone specific image where an echo time TE when water and fat signals are substantially in-phase is used, and the acquired magnetic resonance image may be expressed according to the following equation:

$$S=(W+F+Ie^{i\theta})P$$

where $\theta$ is determined with an image-based pre-calibration for the echo time TE as a phase discontinuity of a known silicone-only image region and a neighboring known water or fat only image region, and P ($\equiv e^{i\phi}$) is a phase factor for the image S. Vector image A may be set to S and vector image B may be set to $Se^{-i\theta}$. A sequenced region growing may be used to construct a vector image V from the two vector images A and B, the vector image V may be used to phase correct or remove P from S to form S', and a silicone-only image and a silicone-suppressed image may be generated according to:

$$I=\text{Imag}\{S'\}/\sin \theta$$

$$W+F=\text{Real}\{S'-I \cos \theta\}$$

where Real{ ... } and Imag{ ... } are to take the real and imaginary components of their component, respectively.

In other respects, embodiments may involve acquiring an inversion recovery image at an inversion recovery time T1 and the image may be expressed according to the following equation:

$$S=Ie^{i\theta}$$

where I is a signal magnitude and $\theta$ is a measured signal phase that comprises a background or error phase and an intrinsic signal phase. Vector image A may be set to S and vector image B may be set to $-S$. A sequenced region growing may be used to construct a vector image V from the two vector images A and B, the vector image V may be used to phase correct the image S, and the phase corrected image S may be displayed and archived as a phase sensitive inversion recovery image.

In other respects, embodiments may involve any apparatuses or systems configured to perform one or more steps disclosed herein in any combination, using for example one or more processors and memory devices coupled to imaging equipment. In still other respects, embodiments may involve software configured to perform one or more steps disclosed herein in any combination.

Other features and associated advantages will become apparent with reference to the following detailed description of specific, example embodiments in connection with the accompanying drawings.

BRIEF DESCRIPTION OF THE DRAWINGS

The following drawings form part of the present specification and are included to further demonstrate certain aspects of disclosed embodiments. The drawings do not limit the invention but simply offer examples.

DESCRIPTION OF ILLUSTRATIVE EMBODIMENTS

The present invention includes methods, systems, apparatuses, and non-transitory computer readable media that can make use of efficient and robust phase correction algorithms, which can be applied to applications such as, but not limited to, all types of phase sensitive MRI. One application used for illustration here is a 2PD (2-point Dixon) technique with a commercially available fast gradient-echo dual-echo data acquisition pulse sequence and a phase-correction algorithm to produce higher resolution images taken from an MRI scan. In other embodiments, a phase correction algorithm according to embodiments of this disclosure may be used in applications such as, but not limited to, one-point Dixon (1PD) techniques for water and fat imaging, one-point Dixon (1PD) techniques for silicone-specific imaging, and phase sensitive inversion recovery imaging. For Dixon chemical shift imaging, a phase correction algorithm according to embodiments of this disclosure may be applied to data collected with different types of pulse sequences, such as conventional spin echo pulse sequences and fast spin echo pulse sequences. The data collected may be from a two-dimensional acquisition or from a three-dimensional acquisition. The data collected may also be from time-series studies such as when used to study contrast agent uptake behavior after a contrast agent is injected into a patient. Alternatively, the data may be acquired with partially parallel imaging techniques such as the sensitivity encoding (SENSE) technique. In these embodiments, after the reconstruction of the acquired images, techniques are provided for correcting background or error phase that may arise as a result of field inhomogeneity or other system imperfections.

In one respect, phase-correction algorithms according to embodiments of this disclosure involve a particular type of sequenced region growing process. The sequence of the region growing may be determined using a quality metric of seed pixels, and selection of the seed pixels may be automatically sorted-out using a series of pixel stacks that bin and hold the seed pixels. The direction for the phase vector of each of the pixels may be determined from an estimated direction using both the amplitude and the phase of the phase vectors of those pixels already determined and that are located within a neighboring area, such as an area defined by a boxcar in two-dimensions or by a regular cuboid in three-dimensions, typically centered around a pixel under consideration. Other shapes and various sizes—fixed and adaptively adjusted—can reflect a suitable neighboring area.

Figure 1:
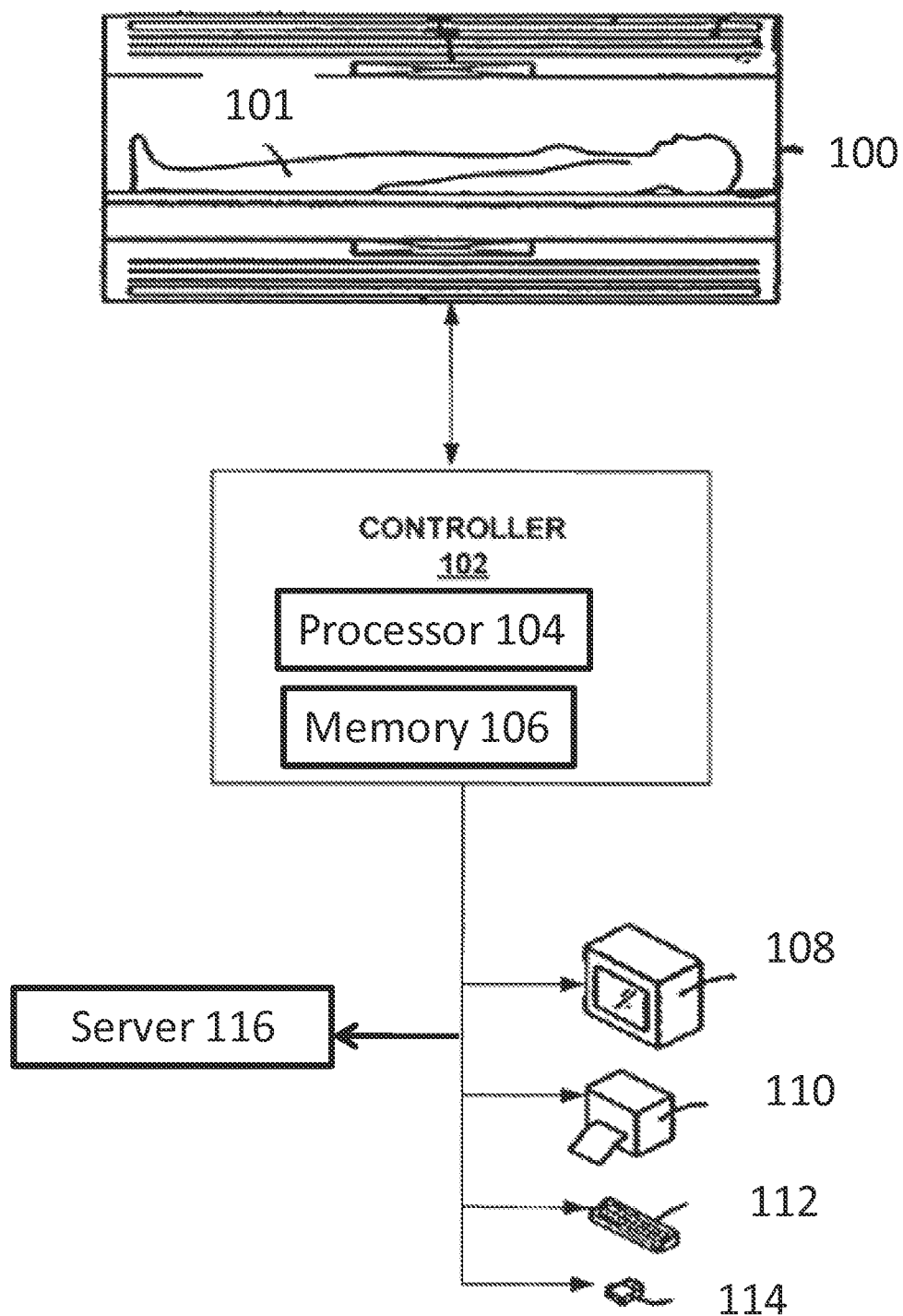
FIG. 1 is an illustration of an MRI apparatus and system in accordance with embodiments of this disclosure.

In FIG. 1, an MRI apparatus, in accordance with an embodiment of the present disclosure, is presented. The MRI apparatus includes a scanner 100, a controller 102, a processor 104, a memory 106, output devices such as a display screen 108, an output printing device 110, and input devices such as a keyboard 112 and a mouse 114. A server 116 may also be included that may communicate with controller 102 and input and output devices such as keyboard 112 and mouse 114. The server 116 and the controller 102 may comprise one or more processors such as processor 104 coupled to, and in communication with, one or more memories such as memory 106. The server 116 may be coupled to the controller 102, and such coupling may be through intermediate devices or a network connection, such as the Internet, or otherwise.

In certain embodiments of this disclosure, error phase correction may be implemented through the use of, for example, processor 104 and memory 106 in the controller 102 or associated with the server 116.

Techniques of the present disclosure may be applied to certain, existing MRI hardware commercially available or known in the art through appropriate programming or data processing techniques, as will be understood to those having ordinary skill in the art, and further as described herein.

In one embodiment, a patient 101 may be placed inside scanner 100. The controller 102 may control aspects of imaging and obtain data, process the data to obtain desired image(s), and output final image(s) to an output device of choice, such as a display screen 108, printing device 110, an electronic storage (local or distant via, for example, a network connection). Images may also be transmitted through a network connection to server 116. Other transmission techniques known in the art may also be utilized.

Two-Point Dixon Water and Fat Imaging

Representing one group of embodiments, the following discloses a signal model and mathematics suitable for two-point Dixon water and fat imaging techniques using flexible echo times, among other applications as will be apparent to those having ordinary skill in the art.

Two raw images acquired at echo times TE1 and TE2 may be expressed as:

$$S_1 = (W + \delta_1 F e^{i\theta_1}) P_1 \quad [1]$$

$$S_2 = (W + \delta_2 F e^{i\theta_2}) P_1 P \quad [2]$$

in which W and F represent the amplitudes of water and fat, respectively. $(\delta_1, \delta_2)$ and $(\theta_1, \theta_2)$ are the amplitude attenuation factors and chemical shift-related phases of fat at TE1 and TE2, respectively. $P_1$ is the phasor (defined as a complex number with a unit amplitude) of the image $S_1$ and includes the effects of all of its phase factors (e.g., magnetic field inhomogeneity) except that of the chemical shift of fat. P is an additional phasor of $S_2$ relative to $S_1$. For given TE1/TE2, $(\delta_1, \delta_2)$ and $(\theta_1, \theta_2)$ can be considered known parameters via an image-based precalibration without assuming any specific spectral model or resorting to measurements by magnetic resonance spectroscopy (described below).

The following can be calculated using Eqs. [1-2]:

$$M_1 = (W^2 + \delta_1^2 F^2 + 2\delta_1 WF \cos \theta_1) \quad [3]$$

$$M_2 = (W^2 + \delta_2^2 F^2 + 2\delta_2 WF \cos \theta_2) \quad [4]$$

in which $M_1 = |S_1|^2$ and $M_2 = |S_2|^2$.

Analogous to Berglund et. al., (Magnetic Resonance in Medicine 65:994-1004 (2011)), one may define:

$$Q = \frac{W}{W + F} \quad [5]$$

which represents the water fraction for a given image pixel.

Eqs. [3 and 4] can be rewritten as:

$$\frac{M_1 M_2}{(W+F)^2} = \left[\left(\frac{W}{W+F}\right)^2 + \delta_1^2 \left(\frac{F}{W+F}\right)^2 + 2\delta_1 \cos\theta_1 \frac{WF}{(W+F)^2}\right] M_2 \quad [6]$$

$$\frac{M_1 M_2}{(W+F)^2} = \left[\left(\frac{W}{W+F}\right)^2 + \delta_2^2 \left(\frac{F}{W+F}\right)^2 + 2\delta_2 \cos\theta_2 \frac{WF}{(W+F)^2}\right] M_1 \quad [7]$$

Combining Eqs. [6 and 7] and recognizing that $$1 - Q = \frac{F}{W+F}$$

one gets:

$$[(1+\delta_2^2 - 2\delta_2 \cos\theta_2) M_1 - (1+\delta_1^2 - 2\delta_1 \cos\theta_1) M_2] Q^2 - 2[(\delta_2^2 - \delta_2 \cos\theta_2) M_1 - (\delta_1^2 - \delta_1 \cos\theta_1) M_2] Q + [(M_1 \delta_2^2 - M_2 \delta_1^2)] = 0 \quad [8]$$

This is a quadratic equation for Q. One may define:

$$\alpha_1' = [(1+\delta_2^2 - 2\delta_2 \cos\theta_2) M_1 - (1+\delta_1^2 - 2\delta_1 \cos\theta_1) M_2] \quad [9]$$

$$\alpha_2' = -2[(\delta_2^2 - \delta_2 \cos\theta_2) M_1 - (\delta_1^2 - \delta_1 \cos\theta_1) M_2] \quad [10]$$

$$\alpha_3' = [(M_1 \delta_2^2 - M_2 \delta_1^2)] \quad [11]$$

Eq. [8] can be rewritten as:

$$\alpha_1' Q^2 + \alpha_2' Q + \alpha_3' = 0 \quad [12]$$

which has the following two mathematically possible solutions:

$$Q_{A,B} = \frac{-a'_2 \pm \sqrt{a'^2_2 - 4a'_1 a'_3}}{2a'_1} = \frac{a_2 \pm \sqrt{a_3}}{a_1} \quad [13]$$

in which:

$$a_1 = a'_1 = [(1+\delta_2^2 - 2\delta_2\cos\theta_2)M_1 - (1+\delta_1^2 - 2\delta_1\cos\theta_1)M_2] \quad [14]$$

$$a_2 = -\frac{a'_1}{2} = [(\delta_2^2 - \delta_2\cos\theta_2)M_1 - (\delta_1^2 - \delta_1\cos\theta_1)M_2] \quad [15]$$

$$a_3 = \frac{a'^2_2 - 4a'_1 a'_3}{4} \quad [16]$$
$$= \begin{bmatrix} (\delta_1^2 + \delta_2^2 - 2\delta_1\delta_2\cos\theta_1\cos\theta_2) \\ M_1 M_2 - \delta_2^2\sin^2\theta_2 M_1^2 - \delta_1^2\sin^2\theta_1 M_2^2 \end{bmatrix}$$

In general, only one of the two solutions in Eq. [13] corresponds to the true and physical solution for the water fraction Q.

Determining the true and physical solution for the water fraction Q for all the pixels of an image is in general a very challenging problem. Here, a particular type of novel sequenced region growing based phase correction may be used to obtain solutions. At this point, selecting the true and physical solution for Q from the two sets of choices in Eq. [13] requires consideration of the phase of the acquired signals (which is removed in Eqs. [3] and [4] by the absolute value operation).

For this purpose, Eqs. [1-2] can be combined to yield the following:

$$S_1^* S_2 = (W + \delta_1 F e^{-i\theta_1})(W + \delta_2 F e^{i\theta_2}) P \quad [17]$$

Dividing Eq. [17] by $(W+F)^2$, one gets:

$$\frac{S_1^* S_2}{(W+F)^2} = [Q + \delta_1(1-Q)e^{-i\theta_1}][Q + \delta_2(1-Q)e^{i\theta_2}]P \quad [18]$$

Using the two solutions from Eq. [13], the following two vectors can be formed:

$$A = S_1^* S_2 [Q_A + \delta_1(1-Q_A)e^{i\theta_1}][Q_A + \delta_2(1-Q_A)e^{-i\theta_2}] \quad [19]$$

$$B = S_1^* S_2 [Q_B + \delta_1(1-Q_B)e^{i\theta_1}][Q_B + \delta_2(1-Q_B)e^{-i\theta_2}] \quad [20]$$

The amplitudes of A and B are to the $2^{nd}$ power order of W and F. For the following processing, they can be weighted differently, e.g., to be approximately linearly proportional to W and F to form a new set of A and B:

$$A' = \frac{A}{|A|}\sqrt{M_1 + M_2} \quad [21]$$

$$B' = \frac{B}{|B|}\sqrt{M_1 + M_2} \quad [22]$$

Other forms of weighting can also be used if desired, as will be recognized by those having ordinary skill in the art. Here, note that the direction represented by either A' or B' will be substantially equal to that represented by P depending on whether the correct, true physical solution for Q is represented by $Q_A$ or $Q_B$ in Eqs. [19-20].

Because P is determined by underlying factors (e.g., magnetic field inhomogeneity) that are generally assumed to be spatially smooth, the correct distribution of P can be determined by constructing a vector field V (initially set to zero for all of the pixels) that is spatially smooth in its angular orientation and represented by either A' or B' on a pixel basis.

Again, in general, constructing such a vector field may be a very challenging problem, especially considering the large variations of the types and qualities of the images encountered in medical imaging. For optimized processing reliability, one may generally use a particular type of sequenced region-growing scheme according to the present disclosure; such a sequenced region-growing process may include the following steps.

First, selecting an initial seed pixel or pixels and assigning either A or B of the initial seed pixel or pixels as a value of V for the initial seed pixel or pixels.

Second, selecting a secondary seed pixel and selecting either A or B of the secondary seed pixel as a value of V for the secondary seed pixel based on whether A or B of the secondary seed pixel has a smaller angular difference with an estimated V for the secondary seed pixel. In one embodiment, the estimated V for a secondary seed pixel is a zeroth order estimation calculated as an average or sum of V for pixels located within a neighboring region of the secondary seed pixel and for which V has been previously determined. In this case, the two angular differences may be conveniently calculated as follows:

$$\alpha_{A V} \leq |\text{angle}(A'^* (\Sigma V)^*)| \quad [23]$$

$$\alpha_{B V} \leq |\text{angle}(B'^* (\Sigma V)^*)| \quad [24]$$

where summation is performed over a group of pixels that lie within a boxcar or cuboid neighborhood of the secondary seed pixel and whose values of V have been previously decided in the sequenced region growing process. The size of the boxcar can be either fixed or adaptively adjusted (see the step below). The value of V for the secondary seed pixel will be set either to its A' or B' depending on which of the two phase differences by Eqs. [23-24] is smaller. For example, if $\alpha_{A V} < \alpha_{B V}$, the value of V for the secondary seed pixel will be set its A'.

Third, a local quality metric may be determined by calculating two angular differences between A' and B' for each of the seed's nearest neighbor pixels (whose value of V is still zero because it has not yet been processed as a seed pixel) with an estimated V of the same nearest neighbor pixel. In one embodiment, the estimated V for a nearest neighbor pixel is a zeroth order estimation calculated as an average or sum of V for pixels located within a neighboring region of the nearest neighbor pixel and for which V has been previously determined. In this case, the two angular differences may be conveniently calculated as follows:

$$\beta_{A V} \leq |\text{angle}(A'^* (\Sigma V)^*)| \quad [25]$$

$$\beta_{B V} \leq |\text{angle}(B'^* (\Sigma V)^*)| \quad [26]$$

where summation is again performed over a group of pixels that lie within a boxcar or cuboid neighborhood of the nearest neighbor pixel and whose values of V have been previously decided in the region growing process. The boxcar size can be either the same or different from that used in Eqs. [23-24].

One difference between the calculations in Eqs. [23-24] and in Eqs. [25-26] is that the calculation in Eqs. [25-26] will include the V of the seed pixel, which is now decided after the second step. The smaller of the two phase differences by Eqs. [25-26] may then used as a quality metric to decide where the nearest neighbor pixel is placed onto a stack (or bin, or other comparable storage or sorting technique) by comparing the smaller of the two phase differences with a maximum possible range of 0 to $\pi$. Among a series of prioritized and initially-empty pixel stacks, the nearest neighbor pixel may be stored in a high or low priority pixel stack if the smaller of the two phase differences is small or large (when compared to the range of 0 to $\pi$), respectively.

Once all the nearest neighbor pixels of the secondary seed pixel have been considered, a pixel from the pixel stack with the highest priority and at least one unprocessed pixel may be selected as the next "best" new secondary seed pixel, and the same sequenced region growing processing may be repeated until all of the pixels have been processed as a seed pixel and the vector V of all the pixels has been substantially determined Several notes can be made about the sequenced region growing embodiments of the present disclosure.

First, before the initiation of the sequenced region growing, A' and B' may be first corrected with a global linear error phase correction along one or more dimensions such as described in Ma et al, Magnetic Resonance in Medicine, 2008, 60(5):1250, which is incorporated herein by reference. This pre-treatment step may be especially useful when global linear phase errors exist due to echo center shift for two echoes.

Second, two separate sequenced region growing processes may be performed by selecting A' or B' as the value of V for a very initial seed pixel. Two vector maps $V_A$ and $V_B$ may be generated. The correct one is expected to have an overall smoother spatial phase variation. And this condition can be detected by calculating and comparing the following two quantities:

$$T_A = \Sigma |\Sigma V_A| \qquad [27]$$

$$T_B = \Sigma |\Sigma V_B| \qquad [28]$$

in which an image is first divided into sub-images (e.g., a 256×256 image may be divided into images of the size 16×16), and the inner summations in Eqs [27-28] may be performed over all the pixels within each and every subimage. The outer summations in Eqs. [27-28] may be performed over all the sub-images. If $T_A > T_B$, then $V_A$ is determined to be the correct V. On the other hand, if $T_A < T_B$, then $V_B$ is determined to be the correct V.

Third, a "quality" of the sequenced region growing process can be monitored and recorded using a quality index which records the pixel stack number or the quality metric of each seed pixel when it is selected as a seed as a function of the sequenced growing sequence. During the sequenced region growing process, the "quality" index can be used to apply enhanced processing selectively only to pixels that are prone to errors in the processing. For example, pixels that are in low priority pixel stacks have small phase variation and may not need the enhanced processing. Conversely, pixels that are in very high priority pixel stacks have very large phase variations and therefore are likely to correspond to background noise and also may not need enhanced processing. Pixels that are in intermediate priority pixel stacks may be prone to errors, and enhanced processing may therefore be helpful.

One type of enhanced processing that can optionally be applied for those pixels that have an intermediate "quality" index is to maximize the amplitude of the local vector summation of the alternative solutions (i.e., A or B) for the vector V:

$$Z = |\Sigma V| \qquad [29]$$

in which the summation is performed over the pixels that have been processed by the sequenced region growing and lie within a small boxcar or cuboid region. Z is maximized by testing A or B as the correct solution of V for those pixels. For example, if Z is bigger when A is used for a pixel than when B is used, then A will be selected as the correct solution of V. Alternatively, the quality index can be used to detect potentially unreliable steps of the sequenced region growing. For example, when the sequenced region growing is crossing noisy regions between two disconnected tissues in an image (e.g., an image of two legs acquired in an axial plane), the quality index is expected to record large variations due to the random fluctuation of noise. Phase correction among the different disconnected tissues can be made consistent by using the quality index to automatically segment an image into segments of consistent region growing. Different segments can then be made consistent by testing alternative solutions from the different segments on a region-level.

Fourth, as indicated previously, the entire region growing process can be generalized to be 3-dimensional in space or even to the time dimension.

After the vector image V is determined by the sequenced region growing embodiments of this disclosure, it can be low-pass filtered. The phasor P can then be taken as a normalized V and removed from Eq. [2]. The corrected Eq. [2] can then be combined with Eq. [1] to solve for $WP_1$ and $FP_1$. Because $P_1$ is also expected to be spatially smooth in its angular orientation, $WP_1$ and $FP_1$ can be low-pass filtered to obtain $\overline{WP_1}$ and $\overline{FP_1}$ and then the SNR-optimized W and F:

$$W = \text{Real}\{(WP_1)\overline{WP_1}^*/|\overline{WP_1}|\} \qquad [30]$$

$$F = \text{Real}\{(FP_1)\overline{FP_1}^*/|\overline{FP_1}|\} \qquad [31]$$

Image-Based Pre-Calibration of the Fat Signal Model

Pre-calibration of the dependence of $(\delta_1, \delta_2)$ and $(\theta_1, \theta_2)$ on $TE_1$ and $TE_2$: The dependence of $(\delta_1, \delta_2)$ and $(\theta_1, \theta_2)$ on $TE_1$ and $TE_2$ can be affected by many factors such as the spectral complexity of fat and pulse sequence related scan parameters such as repetition time (TR) and flip angle as well as the magnetic field strength that is used for imaging. Further, different spectral components of fat not only have different resonance frequencies and relative amplitudes, but may also have different relaxation time constants. Because of this complexity, an image-based pre-calibration procedure may be used to account for all these factors in one embodiment.

In this embodiment, one can determine $(\theta_1, \theta_2)$ as a function of TE by measuring the phase discontinuity between a known water-dominant region (e.g., muscle) and a known neighboring fat-dominant region (e.g., subcutaneous fat). One can determine $(\delta_1, \delta_2)$ as a function of TE by measuring the image intensity variation of a fixed known fat-dominant region (e.g., subcutaneous fat). Because fat in different subjects or anatomical locations is known to have very similar compositions, only one in vivo calibration may be required to account for the effects of complex fat spectra. Different calibrations can be performed to account for other contributing factors (e.g., vastly different scan protocols or field strengths). These image-based pre-calibration results can then be stored in a look-up table or fitted to one or more functions to be used in the phase correction algorithm.

Single Point Dixon Water and Fat Imaging and Single Point Dixon Silicone Imaging In a single point Dixon water and fat imaging application, an image is acquired at a flexible echo time TE, and the image may be expressed as $$S=(W+Fe^{i\theta})P$$

where θ is dependent on TE and the dependence may determined with an image-based pre-calibration, and P ($\equiv e^{i\Phi}$) is the phase factor for the image S. In this case, the vector image A may be equal to S and the vector image B may be equal to $Se^{-i\theta}$. The same sequenced region growing scheme as described above may then be performed on A and B to construct a vector image V. The vector image V is used to phase correct or remove P from S to form S', and a water-only image and a fat-only image are generated according to:

$$F=\text{Imag}\{S'\}/\sin\theta$$

$$W=\text{Real}\{S'-F\cos\theta\}$$

where Real{ ... } and Imag{ ... } are to take the real and imaginary components of their component, respectively.

Additionally, silicone-specific imaging using a single-point Dixon technique can be accomplished where an image is acquired at an echo time TE when water and fat signals are substantially in-phase and the image is represented as:

$$S=(W+F+Ie^{i\theta})P$$

where θ is determined with an image-based pre-calibration for this chosen TE, and P ($\equiv e^{i\Phi}$) is the phase factor for the image S. In this case, vector image A is equal to S and vector image B is equal to $Se^{-i\theta}$.

The sequenced region growing scheme may then be performed on A and B to construct a vector image V. The vector image V is used to phase correct or remove P from S to form S', and a silicone-only image and a silicone-suppressed image are generated according to:

$$I=\text{Imag}\{S'\}/\sin\theta$$

$$W+F=\text{Real}\{S'-I\cos\theta\}$$

where Real{ ... } and Imag{ ... } are to take the real and imaginary components of their component, respectively.

Phase Sensitive Inversion Recovery Imaging

Using an inversion recovery technique an image may be acquired at a certain inversion recovery time T1 and the image may be represented as:

$$S=Ie^{i\theta}$$

where I is the signal magnitude and θ is the measured signal phase that comprises a background or error phase and an intrinsic signal phase. In this case, the vector image A is S and the vector image B is −S.

The sequenced region growing scheme may then be performed on A and B to construct a vector image V. The vector image V is used to phase correct or remove P from S, and the phase corrected image S is displayed or archived as a phase sensitive inversion recovery image.

* * *

Figure 2A:
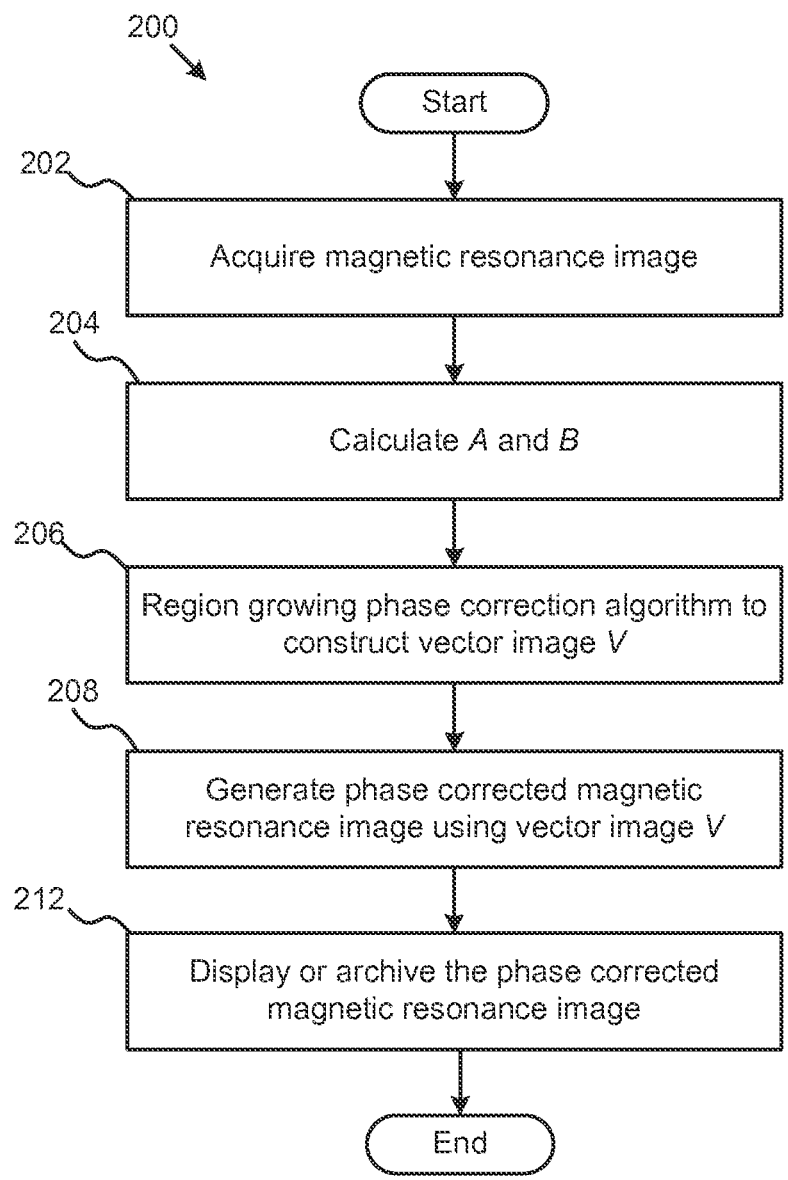
FIGS. 2A and 2B are flow charts illustrating phase correction steps in accordance with embodiments of this disclosure.

FIG. 2A is a flowchart of image processing steps 200 according to embodiments of the present disclosure. Steps 200 may be used to generate a phase corrected magnetic resonance image and may follow any one or more of the calculations noted above. These steps—or any steps disclosed here—may be performed on a suitable processor such as processor 104 of FIG. 1. The processor, in turn, may be coupled to, or associated with memory 106, controller 102, or server 116.

In step 202, a magnetic resonance image containing background or error phase information is acquired. Such information may be provided by MRI equipment such as that shown in FIG. 1 or otherwise. In step 204, two vector images A and B are calculated using the acquired image or images so that a vector orientation by one of the two vector images at a pixel is substantially determined by the background or error phase at the pixel, and the vector orientation at the pixel by the other vector image is substantially different from that determined by the background or error phase at the pixel.

In step 206, a sequenced region growing phase correction algorithm is applied to the vector images A and B to construct a new vector image V. A global linear phase correction, or other corrections, can be applied prior to the region growing phase correction algorithm.

In step 208, the phase corrected magnetic resonance image or images are generated from the acquired magnetic resonance image or images using the vector image V. In step 212, the phase corrected magnetic resonance image or images are displayed or archived. Display or archiving may be done in conjunction with the equipment of FIG. 1 or any display device known in the art, including but not limited to devices that produce electronic or hard-copy output, as well as network-connected devices.

Figure 2B:
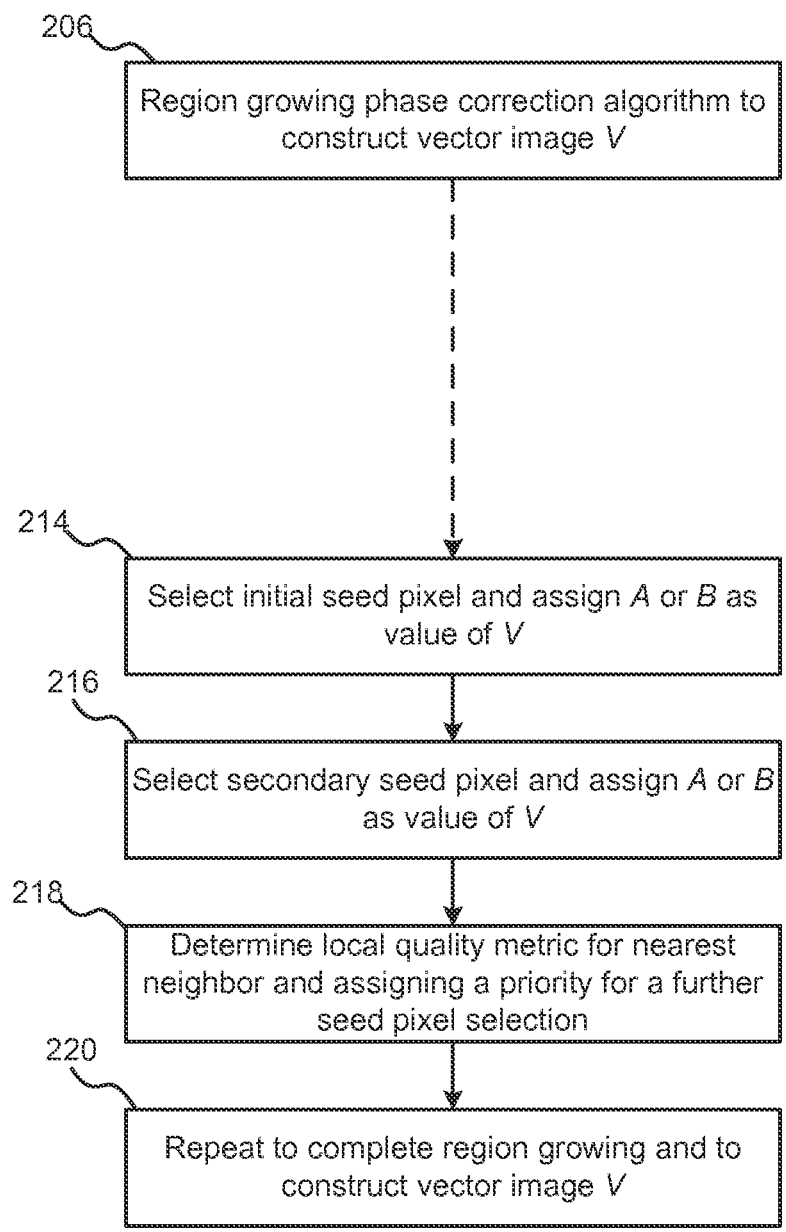

FIG. 2B is a flowchart that is an extension of FIG. 2A and also reflects steps 200. FIG. 2B expands step 206 of FIG. 2A according to certain embodiments of this disclosure. Steps 200 as reflected in FIG. 2B may be used to generate a phase corrected magnetic resonance image or images and may follow any one or more of the calculations noted above. These steps—or any steps disclosed here—may be performed on a suitable processor such as processor 104 of FIG. 1. The processor, in turn, may be coupled to, or associated with memory 106, controller 102, or server 116.

In step 214, an initial seed pixel or pixels are selected and either A or B of the initial seed pixel or pixels is assigned as a value of V for the initial seed pixel or pixels. In step 216, a secondary seed pixel is selected and either A or B of the secondary seed pixel is selected as a value of V for the secondary seed pixel based on whether A or B of the secondary seed pixel has a smaller angular difference with an estimated V for the secondary seed pixel. In step 218, a local quality metric is determined for nearest neighbor pixels of the secondary seed pixel for which V has not been determined; and, a priority of a nearest neighbor pixel is determined using this local quality metric so that one may determine the sequence by which the nearest neighbor pixel is to be selected as a further seed pixel. Step 220 reflects that steps 214 and 216 may be repeated to complete this sequenced region growing with respect to further seed pixels and to construct vector image V so that a vector orientation of V at each pixel is substantially determined by the background or error phase at the pixel.

Figure 3:
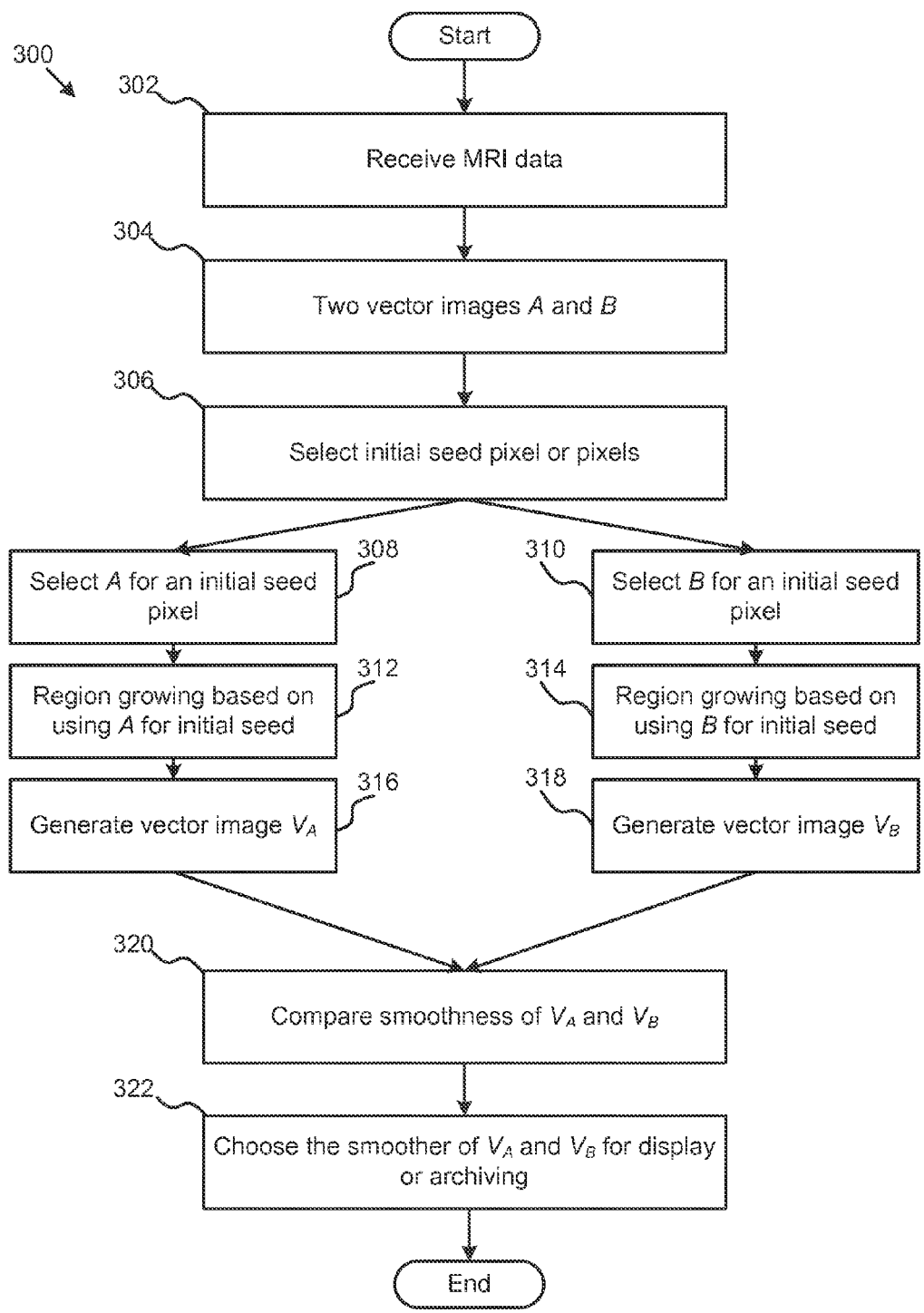
FIG. 3 is another flow chart illustrating phase correction steps in accordance with embodiments of this disclosure.
Figure 4:
FIGS. 4-7 are water- and fat-only images generated and displayed in accordance with examples of this disclosure.
Figure 5:
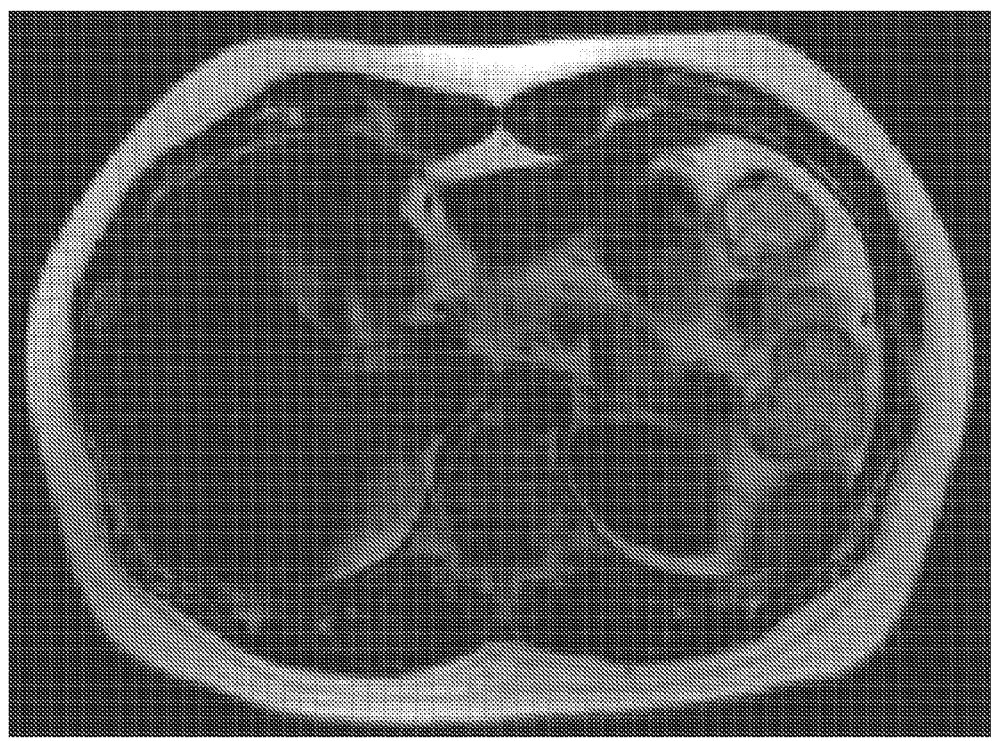
Figure 6:
Figure 7:
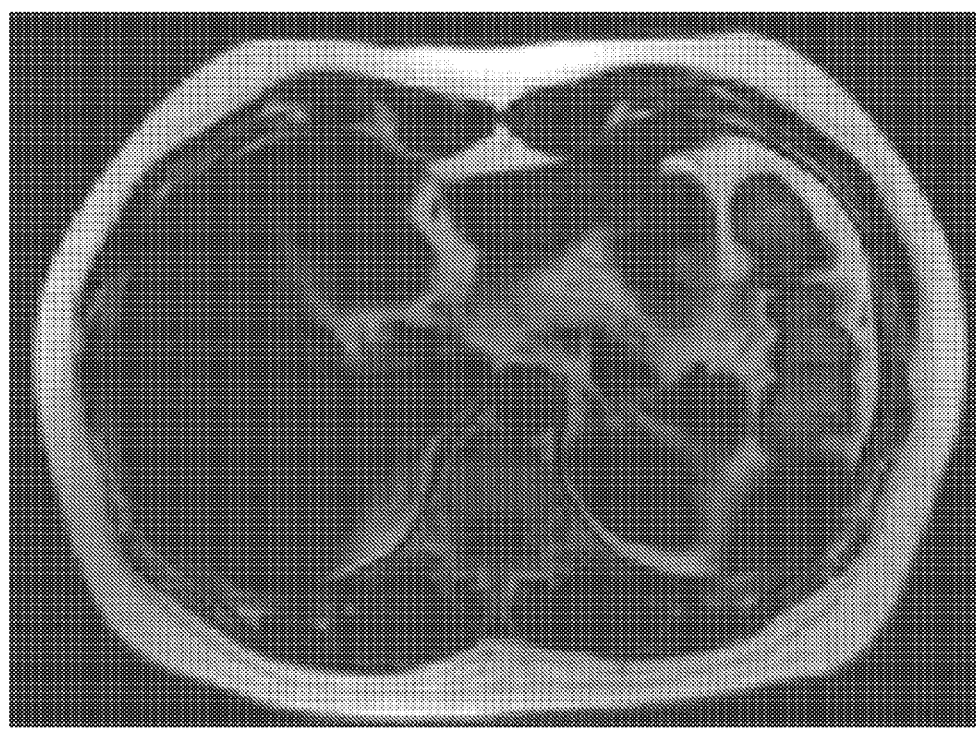

FIG. 3 is a flowchart of image processing steps 300 according to embodiments of the present disclosure. In step 302, MRI image data is obtained (e.g., from scanning a patient 101). In step 304, two vector images A and B are reconstructed from the received MRI data from step 302. An initial seed pixel or pixels are selected in step 306. An initial seed pixel may be selected randomly, or one or more seed pixels may be selected according to an algorithm or a predetermined sequence. A branch may be taken after step 306.

In step 308, vector image A is selected for an initial seed pixel, and in step 310 vector image B is selected for the initial seed pixel.

Calculations in the separate branches may be done serially, in parallel, or in some combination of either. In each branch a sequenced region growing process as disclosed herein may be performed as illustrated in steps 312 and 314.

A vector image $V_A$ is formed in step 316 after processing all or a sufficient subset of pixels, and a vector image $V_B$ is formed in step 318 after processing all or a sufficient subset of pixels.

The smoothness of $V_A$ and $V_B$ are compared in step 320, and the smoother of the two vector images may be chosen in step 322 as the vector V, which is then used to phase correct the acquired image or images and to generate phase corrected magnetic resonance image or images for display or storage purposes.

Any type of MRI image or images may be subjected to image processing steps 200 or 300, or those disclosed herein. Again, a suitable MRI image or images may involve two point Dixon water and fat images that are acquired using flexible echo times. Image processing steps 200 and 300 may be performed by—and may be integrated with, either by hardware or software—any suitable MRI system, including commercially available systems. Similarly the processing steps of this disclosure may be implemented on a non-transitory computer readable storage medium as an executable program that instructs a microprocessor to perform the steps.

* * *

The following examples are included to demonstrate aspects of specific experiments related to this disclosure. Subject matter presented as an example may be encompassed by the present claims or added to the claims to define protected subject matter.

EXAMPLE 1

Two-Point Dixon Example

The flexible phase postprocessing strategy, as described in detail above, was implemented using MATLAB (MathWorks), and a 3D fast spoiled gradient-echo bipolar dual echo pulse sequence was used to collect raw data for a water/fat phantom (consisting of water and vegetable oil) and for the in vivo abdomen of a human subject using a 1.5T whole-body MR scanner (GE Healthcare; HDxt platform). For the in vivo imaging, an eight-channel phased array body coil was used, and the scan parameters were as follows: TR=minimum, FOV=36×27 cm, acquisition matrix=256× 192, flip angle=12°, slice thickness=4 mm, total number of slices=38, and receiver bandwidth=±83.33 kHz. Minimum as well as different combinations of manually selected echo times were used for the dual-echo readout. For the phantom imaging, an eight-channel phased array head coil and scan parameters similar to those for the in vivo scanning were used except that for a fixed TE1 of 1.2 ms, TE2 varied systematically from 2.9 ms (minimum allowed) to 5.2 ms with a ATE of 0.1 ms; for a fixed TE2 of 4.6 ms, TE1 varied systematically from 1.2 ms to 2.9 ms (maximum allowed) with a ATE of 0.1 ms.

Before Dixon processing, $(\theta_1, \theta_2)$ can be determined as a function of TE by measuring the phase discontinuity between a known water-dominant region (e.g., muscle) and a known neighboring fat-dominant region (e.g., subcutaneous fat). $(\delta_1, \delta_2)$ can also be determined as a function of TE by measuring the image intensity decay of a fixed fat dominant region. Because fat in different subjects or anatomical locations is known to have very similar compositions, only one in vivo calibration is required to account for the effects of complex fat spectra. Different calibrations may be performed to account for other contributing factors (e.g., vastly different scan protocols or field strengths). The extended phase correction algorithm was able to reconstruct separate water and fat-only images of both the phantom and abdomen in vivo for all of the selected TE1/TE2 combinations.

For example, FIGS. 4-7 show two sets of water- and fat-only images for data acquired at TE1/TE2=1.5/3.4 ms with a corresponding precalibrated $(\theta_1, \theta_2)$ of (77°, 245°) (FIG. 4, FIG. 5) and at TE1/TE2=2.2/4.4 ms with a corresponding precalibrated $(\theta_1, \theta_2)$ of (140°, 305°) (FIG. 6, FIG. 7) that are closer to being out-of-phase/in-phase. The water/fat separation and overall image quality are excellent in both cases. However, the first set of data required shorter TR and scan times (5.5 ms and 21 s, respectively) than those for the second set of data (6.5 ms and 25 s, respectively) for otherwise identical scan parameters.

The sequenced region growing-based phase correction strategy can be implemented as a fully automatic solution, and it is capable of robust water and fat separation using two input images with flexible echo times. Because of this increased flexibility, note that the less-efficient dual-echo image acquisition with unipolar flyback readout gradients may be used as a practical alternative to the more-efficient bipolar acquisition for its advantage of having no off-resonance related spatial misregistration between the two input images along the frequency-encode direction.

It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements. For example, different schemes of selecting the initial seed pixel or pixels and assigning the value of V for these initial seed pixels may be employed; Different ways of calculating the vector images A and B are possible and can be used for the two point Dixon imaging with flexible echo times or other phase sensitive magnetic resonance imaging applications; The phase correction algorithm with the sequenced region growing can also be easily extended to applications in which more than two vectors images (e.g., A, B, C) need to be considered to construct a final vector image V that is used for phase correction; Calculation of an estimated V for a pixel may be performed using more complicated method beyond a $0^{th}$ order or $1^{st}$ order estimation; Additionally, calculation of the vector images A and B may be explicit or implicit, and the two vector images may be weighted differently as described herein.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The term program, computing device program, and/or software, as used herein, is defined as a sequence of instructions designed for execution on a computer system. A program may include, for example, a subroutine, a function, a procedure, an object method, an object implementation, and an executable application and/or other sequence of instructions designed for execution on a computer system.

REFERENCES

The following references, and any reference mentioned in this application, are herein incorporated by reference in full:
1. Ma J. MRM 2004; 52(2):415-419.
2. Ma J, et al. JMRI 2006; 23(1):36-41.
3. Xiang Q S. MRM 2006; 56(3):572-584.
4. Eggers H, et al. ISMRM, 2010. p. 770.
5. Eggers H. ISMRM 2010. p. 2924.
6. Berglund et. al., Magnetic Resonance in Medicine 65:994-1004 (2011)
7. U.S. Pat. No. 7,227,359
8. U.S. Pat. No. 7,888,936
9. Eggers H, et al., Magnetic Resonance in Medicine 65(1):96-107, 2011.

The invention claimed is:

1. A computerized method for generating a phase corrected magnetic resonance image or images comprising:
   (a) acquiring a magnetic resonance image or images containing background or error phase information;
   (b) calculating two vector images A and B using the acquired image or images so that a vector orientation by one of the two vector images at a pixel is determined by the background or error phase at the pixel, and the vector orientation at the pixel by the other vector image is different from that determined by the background or error phase at the pixel;
   (c) applying a sequenced region growing phase correction algorithm to the vector images A and B to construct a new vector image V, wherein the algorithm comprises:
      (i) selecting an initial seed pixel or pixels and assigning either A or B of the initial seed pixel or pixels as a value of V for the initial seed pixel or pixels;
      (ii) selecting a secondary seed pixel and selecting either A or B of the secondary seed pixel as a value of V for the secondary seed pixel based on whether A or B of the secondary seed pixel has a smaller angular difference with an estimated V for the secondary seed pixel;
      (iii) determining for the secondary seed pixel a local quality metric for each of the nearest neighbor pixels of the secondary seed pixel for which V has not been determined and assigning a priority to each of the nearest neighbor pixels using the local quality metric in order to determine the sequence by which each of the nearest neighbor pixels is to be selected as a further seed pixel;
      (iv) repeating the steps of (ii) and (iii) to complete the sequenced region growing with respect to further seed pixels and to construct the vector image V so that a vector orientation of V at each pixel is substantially determined by the background or error phase at the pixel;
   (d) generating the phase corrected magnetic resonance image or images from the acquired magnetic resonance image or images using the vector image V; and
   (e) displaying or archiving the phase corrected magnetic resonance image or images.

2. The method of claim 1, wherein an initial seed pixel or pixels are placed onto a high priority pixel stack or stacks among a series of pixel stacks that are initially empty and which facilitate a sequencing of the sequenced region growing.

3. The method of claim 1, wherein a pixel is selected as a secondary seed pixel if it has not been processed previously as a seed pixel and it is on a pixel stack that has a highest priority among pixel stacks that contain at least one pixel that has not been processed as a seed pixel.

4. The method of claim 1, wherein the local quality metric of a pixel is calculated as the smaller of two orientational differences between A and B of the pixel with an estimated V for the pixel.

5. The method of claim 4, wherein the estimated V for a pixel is a zeroth order estimation calculated as an average of V for pixels located within a neighboring region of the pixel and for which V has been previously determined.

6. The method of claim 5, wherein a size of the neighboring region is either fixed or adaptively adjusted based on a local quality metric for the pixel.

7. The method of claim 1, wherein a maximum possible range of $0$-$\pi$ for the angular difference between any two vectors is used to gauge and bin the local quality metric and to place a pixel onto a pixel stack and wherein the pixel stack covering a subrange of $0$-$\pi$ for the quality metric is assigned a priority, and wherein a pixel stack of a higher priority is for receiving pixels with a smaller quality metric and a pixel stack of a lower priority is for receiving pixels with a larger quality metric.

8. The method of claim 7, wherein the priority of a pixel stack from which a pixel is selected as a seed pixel is recorded for the sequenced region growing as a quality metric index to reflect an integrity of the sequenced region growing.

9. The method of claim 8, wherein the quality metric index is used to segment an image into different segments of possible inconsistent region growing and then to combine the different segments into an overall consistent region growing to form a final vector image V.

10. The method of claim 1, wherein a value of the vector A for an initial seed pixel is assigned as $V_A$, and a sequenced region growing is performed to construct a vector image $V_A$, and wherein a value of the vector B for the same initial seed pixel is assigned as $V_B$, and another sequenced region growing is performed to construct a vector image $V_B$.

11. The method of claim 10, wherein either vector image $V_A$ or vector image $V_B$ is set to be a final vector image V, depending on whether vector image $V_A$ or vector image $V_B$ has a greater overall orientational smoothness.

12. The method of claim 1, wherein the sequenced region growing is performed in two or three spatial dimensions or by including the temporal dimension for a series of dynamically acquired images.

13. The method of claim 1 wherein acquiring a magnetic resonance image or images comprises acquiring two-point Dixon water and fat images, wherein a first image S1 is acquired at a first echo time TE1 and a second image S2 is acquired at a second echo time TE2.

14. The method of claim 13, wherein the images $S_1$ and $S_2$ are expressed according to the following equations:

$$S_1 = (W + \delta_1 F e^{i\theta_1}) P_1$$

$$S_2 = (W + \delta_2 F e^{i\theta_2}) P_1 P$$

where W and F are amplitudes for water and fat respectively, $P_1$ is a phase factor of image $S_1$, P is an additional phase factor of image $S_2$ relative to image $S_1$ and is determined by a background or error phase, and the method further comprises calculating an amplitude attenuation factor ($\delta_1$, $\delta_2$) and phase ($\theta_1$, $\theta_2$) as a function of two echo times (TE1, TE2) for the fat signal using a pre-determined fat spectrum.

15. The method of claim 14, wherein the images $S_1$ and $S_2$ are used to generate two vector images A and B as expressed according to the following equations:

$$A = S_1 {}^* S_2 [Q_A + \delta_1(1-Q_A)e^{i\theta_1}]/[Q_A + \delta_2(1-Q_A)e^{-i\theta_2}]$$

$$B = S_1 {}^* S_2 [Q_B + \delta_1(1-Q_B)e^{i\theta_1}]/[Q_B + \delta_2(1-Q_B)e^{-i\theta_2}]$$

where $Q_A$ and $Q_B$ are the two mathematically possible solutions of the following quadratic equation of Q, which is defined as $$Q = \frac{W}{W+F}$$

(i.e., the water fraction for given pixel):

$$[(1+\delta_2^2 - 2\delta_2 \cos\theta_2)M_1 - (1+\delta_1^2 - 2\delta_1 \cos\theta_1)M_2]Q^2 - 2[(\delta_2^2 - \delta_2 \cos\theta_2)M_1 - (\delta_1^2 - \delta_1 \cos\theta_1)M_2]Q + [(M_1\delta_2^2 - M_2\delta_1^2)] = 0$$

where $M_1$ and $M_2$ are the square of the amplitudes of the images $S_1$ and $S_2$, respectively (i.e., $M_1 = |S_1|^2$ and $M_2 = |S_2|^2$.

16. The method of claim 15, wherein the vector image V is used to phase correct and remove the phase factor P from the image $S_2$, the phase corrected $S_2$ is combined with $S_1$ to solve for $WP_1$ and $FP_1$, and then to generate a water-only image and a fat-only image according to the following equations:

$$W = \mathrm{Real}\{(WP_1)\overline{WP_1}{}^*/|\overline{WP_1}|\}$$

$$F = \mathrm{Real}\{(FP_1)\overline{FP_1}{}^*/|\overline{FP_1}|\}$$

where Real{ . . . } is to take the real component of its complex argument, * is to take the complex conjugate of its argument, and $\overline{WP_1}$ and $\overline{FP_1}$ represent low-pass filtering of $\overline{WP_1}$ and $\overline{FP_1}$, respectively.

17. The method of claim 1 wherein acquiring a magnetic resonance image or images comprises acquiring a single-point Dixon water and fat image wherein a flexible echo time TE is used and the acquired magnetic resonance image is expressed as: $S = (W + Fe^{i\theta})P$, where $\theta$ is dependent on TE and the dependence is determined using a pre-determined fat spectrum model, and P ($\equiv e^{i\phi}$) is a phase factor for the image S.

18. The method of claim 1, wherein acquiring a magnetic resonance image or images comprises acquiring a single-point silicone specific image wherein an echo time TE when water and fat signals are substantially in-phase is used, and the acquired magnetic resonance image is expressed according to the following equation:

$$S = (W + F + Ie^{i\theta})P$$

where $\theta$ is determined with an image-based pre-calibration for the echo time TE as a phase discontinuity of a known silicone-only image region and a neighboring known water or fat only image region, and P ($\equiv e^{i\phi}$) is a phase factor for the image S.

19. A system for generating a phase corrected magnetic resonance image or images comprising:
(A) a magnetic resonance imaging controller;
(B) a processor coupled to the controller and configured to execute phase correction instructions applicable to a magnetic resonance image or images, wherein the instructions comprise:
 (a) calculating two vector images A and B associated with an acquired image or images so that a vector orientation by one of the two vector images at a pixel is determined by a background or error phase at the pixel, and the vector orientation at the pixel by the other vector image is different from that determined by the background or error phase at the pixel;
 (b) applying a sequenced region growing phase correction algorithm to the vector images A and B to construct a new vector image V, wherein the sequenced region growing phase correction algorithm comprises:
  (i) selecting an initial seed pixel or pixels and assigning either A or B of the initial seed pixel or pixels as a value of V for the initial seed pixel or pixels;
  (ii) selecting a secondary seed pixel and selecting either A or B of the secondary seed pixel as a value of V for the secondary seed pixel based on whether A or B of the secondary seed pixel has a smaller angular difference with an estimated V for the secondary seed pixel;
  (iii) determining for the secondary seed pixel a local quality metric for each of the nearest neighbor pixels of the secondary seed pixel for which V has not been determined and assigning a priority to each of the nearest neighbor pixels using the local quality metric in order to determine the sequence by which each of the nearest neighbor pixels is to be selected as a further seed pixel;
  (iv) repeating the steps of (ii) and (iii) to complete the sequenced region growing with respect to further seed pixels and to construct the vector image V so that a vector orientation of V at each pixel is substantially determined by the background or error phase at the pixel;
 (c) generating a phase corrected magnetic resonance image or images from the acquired magnetic resonance image or images using the vector image V; and
 (d) displaying or archiving the phase corrected magnetic resonance image or images; and
(C) an output or storage device configured to display or store the phase corrected magnetic resonance image or images.

20. A non-transitory computer readable storage medium with an executable program stored thereon, wherein the program instructs a microprocessor to perform steps comprising:
(a) loading into memory a magnetic resonance image or images;
(b) calculating two vector images A and B associated with the loaded image or images so that a vector orientation by one of the two vector images at a pixel is determined by a background or error phase at the pixel, and the vector orientation at the pixel by the other vector image is different from that determined by the background or error phase at the pixel;
(c) applying a sequenced region growing phase correction algorithm to the vector images A and B to construct a new vector image V, wherein the sequenced region growing phase correction algorithm comprises:
  (i) selecting an initial seed pixel or pixels and assigning either A or B of the initial seed pixel or pixels as a value of V for the initial seed pixel or pixels;
  (ii) selecting a secondary seed pixel and selecting either A or B of the secondary seed pixel as a value of V for the secondary seed pixel based on whether A or B of the secondary seed pixel has a smaller angular difference with an estimated V for the secondary seed pixel;
  (iii) determining for the secondary seed pixel a local quality metric for each of the nearest neighbor pixels of the secondary seed pixel for which V has not been determined and assigning a priority to each of the nearest neighbor pixels using the local quality metric to determine the sequence by which each of the nearest neighbor pixels is to be selected as a further seed pixel;
  (iv) repeating the steps of (ii) and (iii) to complete the sequenced region growing with respect to further seed pixels and to construct the vector image V so that a vector orientation of V at each pixel is substantially determined by the background or error phase at the pixel;
(d) generating the phase corrected magnetic resonance image or images from the acquired magnetic resonance image or images using the vector image V; and
(e) displaying or archiving the phase corrected magnetic resonance image or images.

* * * * *

UNITED STATES PATENT AND TRADEMARK OFFICE
CERTIFICATE OF CORRECTION

PATENT NO. : 9,449,386 B2
APPLICATION NO. : 14/380972
DATED : September 20, 2016
INVENTOR(S) : Jingfei Ma Page 1 of 1

It is certified that error appears in the above-identified patent and that said Letters Patent is hereby corrected as shown below:

In the Claims

In Column 22, Claim 7, Line 24, after "0–π", insert space.

In Column 22, Claim 14, Line 58, delete "$S_i$" and insert --$S_1$-- therefor.

In Column 23, Claim 15, Line 30, delete "$M_2 = |S_2|^2$" and insert --$M_2 = |S_2|^2)$-- therefor.

In Column 23, Claim 16, Line 45, delete "$\overline{WP_1}$ and $\overline{FP_1}$" and insert --$WP_1$ and $FP_1$-- therefor.

Signed and Sealed this
Twentieth Day of June, 2017

Joseph Matal
*Performing the Functions and Duties of the
Under Secretary of Commerce for Intellectual Property and
Director of the United States Patent and Trademark Office*